United States Patent [19]

Appelle

[11] Patent Number: 4,618,325
[45] Date of Patent: Oct. 21, 1986

[54] CUSTOM DENTAL SHADE GUIDE TAB

[76] Inventor: Gerald K. Appelle, 245 E. 87th St., New York, N.Y. 10128

[21] Appl. No.: 713,182

[22] Filed: Mar. 18, 1985

[51] Int. Cl.[4] ............................................. A61C 19/10
[52] U.S. Cl. ......................................... 433/26; 433/40
[58] Field of Search ...................... 433/26, 40; 264/19

[56] References Cited

U.S. PATENT DOCUMENTS

| 2,479,543 | 8/1949 | Russell | 433/26 |
| 2,805,478 | 9/1957 | Adams | 433/26 |
| 3,964,167 | 6/1976 | Yerkes | 433/26 |
| 4,115,922 | 9/1978 | Alderman | 433/26 |
| 4,382,784 | 5/1983 | Freller | 433/26 |
| 4,449,928 | 5/1984 | Weissenfluh | 433/40 |
| 4,500,288 | 2/1985 | Weissenfluh | 433/40 |

FOREIGN PATENT DOCUMENTS 0087022  8/1983  European Pat. Off. ............. 433/40

Primary Examiner—John J. Wilson
Attorney, Agent, or Firm—Bauer & Amer

[57] ABSTRACT

A hollow transparent mold is provided for the custom formation of a dental shade guide. The mold is provided with an opening into which the dentist inserts raw filling material selected from the material he intends using on the patient. The mold is provided with a handle and after hardening of the raw material forms a dental shade guide.

11 Claims, 21 Drawing Figures

CUSTOM DENTAL SHADE GUIDE TAB

BACKGROUND OF THE INVENTION

The present invention relates to a device and method of forming a custom dental shade guide for matching tooth colored filling material to natural teeth.

Dental shade guides serve the purpose of assisting the dentist in matching a filling, restorative material, or artificial tooth to the patient's existing teeth.

Shade guide assemblies generally consist of a holder from which project a plurality of individual color samples or tabs usually in the shape of a tooth. The dentist chooses from among the group the one tab which most precisely matches the tooth to be restored. A restorative material or artificial tooth is then selected that corresponds in shade to the particular tab chosen.

The early design of shade guides contributed to inaccuracies in color match because the shade tabs were not translucent as are natural teeth. They also had to be positioned in the mouth in such a way as to distort the light reaching the tooth. In 1949, Harvey J. Russell designed a shade guide described in U.S. Pat. No. 2,479,543 for the purpose of correcting these shortcomings, which has more or less become the standard since.

The Russell shade guide and all subsequent modifications are made of a material, usually a heat processed acrylic resin, that bears no relation to the tooth colored filling materials used to restore teeth. Today, the cosmetic materials most commonly used for fillings are chemically and physically different from the material of which the colored tab of the shade guide is made. More specifically, these restorative materials differ from the shade tabs in their optical properties and characteristics, that is, the way in which they reflect, refract, and transmit light. It is this difference between the composition of the shade guide tab and that of the filling material itself, which accounts for the greatest source of error in shade selection.

Manufacturers of the various restorative filling materials either provide their own shade guide with the materials they sell or provide a reference to one of the standard shade guides used in selecting artificial teeth. In either case, the actual filling material, being of different composition from the colored portion of the shade guide tab, seldom matches the tab due to the inherent differences in the optical properties of the materials. Furthermore, none of the shade guides indicate what the resulting combination of two or more restorative materials will look like when mixed.

One way around this problem, has been the practice of some dentists to take a sample of the filling material to be used, and place it next to the tooth to be restored, in order to determine if the shade will match. This method eliminates the use of the shade guide. However, if the shade is not correct, the sample material taken from the supply tube must be discarded since the syringe type dispensers of the new filling materials do not provide for material to be replaced once extruded from the tube. This can be a rather costly practice. Furthermore, it is sometimes necessary to obtain the proper shade by mixing two or more different shades of materials. If the resulting color is inadequate, this material also must be discarded.

It is an object of the present invention to provide a device and method which allows the dentist to form the restorative material that he will be using to repair a tooth, directly into a shade tab so as to facilitate an accurate color match.

It is another object of this invention to provide a device and method which utilizes a sample of the filling material itself in forming the colored portion of the shade tab. Since a shade tab thus formed is an exact color match of the filling material and can be used repeatedly for subsequent color matches, it is more practical than the methods being used today.

It is still another object to provide a device and method whereby the individual dentist may form a shade tab for each of the pure colors of filling material generally used by the dentist as well as for selected combinations of filling materials and thereby create a custom shade guide mounted assembly of various shades.

The number of shade combinations that may be incorporated into tabs will increase quantitatively and qualitatively the sample selection from which a dentist may choose an appropriate match between filling material and tooth to be restored and the shade tabs thus formed will be more representative of what can be reproduced from the filling materials on hand.

These objects, advantages and benefits as well as others will be readily apparent from the following disclosure.

SUMMARY OF THE INVENTION

According to the present invention a custom shade tab is produced employing a clear transparent hollow mold, preferably tooth shaped, into which the dentist places the filling material of a given shade or combination of shades. Any number of such tabs of varying shades are produced to be used for future reference in matching the filling material to the natural tooth to be restored. A handle is incorporated into the molded filling material as a means of carrying this material to the mouth.

The handle would be provided with a button or similar anchor to retain the molded material. The handle would be positioned so that its retentive button would project into the mass of filling material within the mold until the material has set hard. Once this has occurred, the handle and molded portion would become joined. The handle could be manufactured as a separate piece to be placed into the material, or alternatively as part of the transparent mold itself, allowing the handle to be bent, folded, or rotated into the material.

Once the material sets, the transparent mold may be stripped away from it leaving the filling material attached to the handle. The handle portion provides an area for identification by code of the particular shade or combination of shades of filling material used to produce the tab. A number of tabs thus produced, of varying shades, are placed side by side in a mount for convenient reference in future shade selection.

Full details of the invention are set forth in the following description and illustrated in the accompanying drawing.

DESCRIPTION OF THE INVENTION

Figure 1:
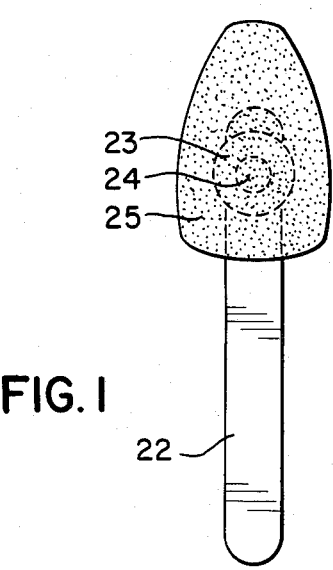
FIG. 1 is a front view of a fully assembled shade guide tab with mold blank removed, formed according to the present invention.
Figure 2:
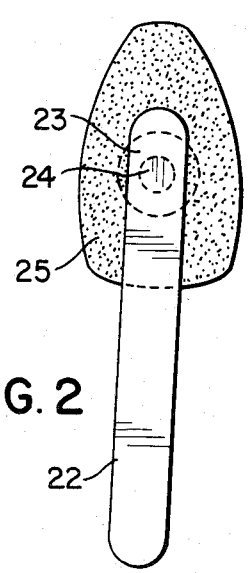
FIG. 2 is a rear view of the device with mold blank removed.
Figure 3:
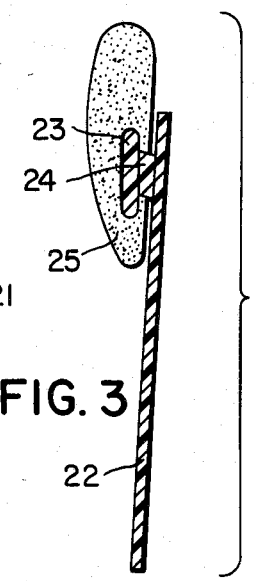
FIG. 3 is a cross-section of the device with mold blank removed.
Figure 4:
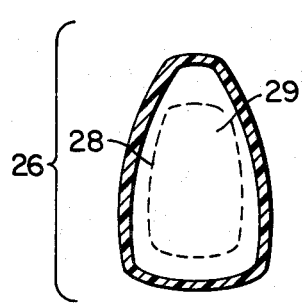
FIG. 4 is a front view through the median plane of a mold blank used in forming the device of FIG. 1.
Figure 5:
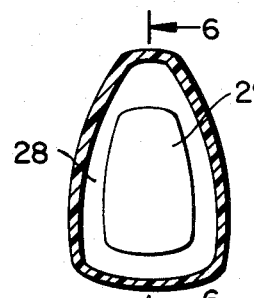
FIG. 5 is a rear view through the median plane of the mold blank.
Figure 6:
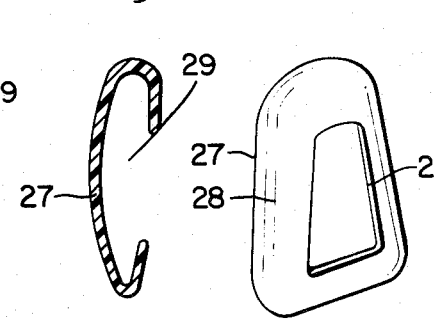
FIG. 6 is a cross-section of FIG. 5 in the direction of the arrows 6—6.
Figure 7:
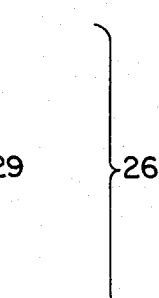
FIG. 7 is a rear perspective view of the mold blank.

A completed custom shade guide tab, generally depicted by the numberal 21 is seen in FIGS. 1, 2 and 3. The tab comprises a handle 22 of generally flat stick-like shape, having an anchor formed integrally therewith at one end, preferably in the shape of a mushroom-like button, having a knob 23 and a narrow post 24. Mounted on the anchor is a head 25 formed from a mass of filling material. The shape of the head of filling material is determined by the shape of the mold blank 26. Although a flat stick-like handle is shown, any other shape may be used. The mold blank and consequently the head of the formed filling material is preferably in the shape of a tooth.

As described herein, the filling material may be any substance used for direct restoration of teeth, most commonly composite macrofil or microfil resins, and glass ionomer cements. The two paste and powder-liquid systems self-polymerize once the components are mixed. Other systems of the single paste type polymerize (harden) when subjected to certain wave lengths of visible or ultraviolet light.

The shade tab is custom fabricated by the dentist who has been initially supplied with the components consisting of a mold blank or shell form (FIGS. 4, 5, 6 & 7) and separate handle (FIGS. 8, 9 & 10) or mold blank and handle combination (FIGS. 13, 14 & 15 or FIGS. 16, 17 & 18).

The first component is a hollow mold blank or shell from of non-reflective, clear, transparent material such as cellulose acetate. Ideally it would be shaped to produce a form resembling an upper incisor tooth. The mold would be ½ mm or less in thickness with a curved front wall 27 continuous with a peripheral lip 28 which flattens toward the rear, terminating in an opening 29, the diameter of which would be large enough to permit entry of the anchor.

Figure 8:
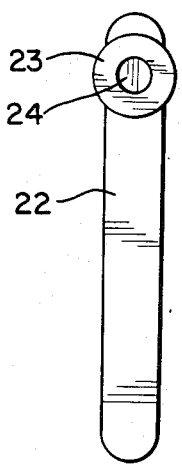
FIG. 8 is, according to FIG. 1, a front view of the handle used in forming the device of FIGS. 1, 2 and 3.
Figure 9:
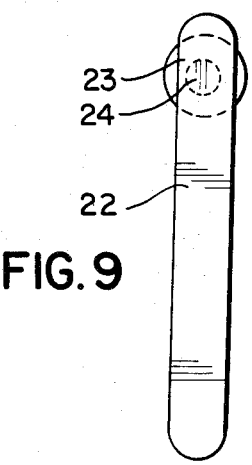
FIG. 9 is a rear view of the handle.
Figure 10:
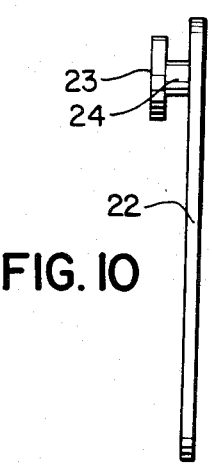
FIG. 10 is a side view of the handle.
Figure 13:
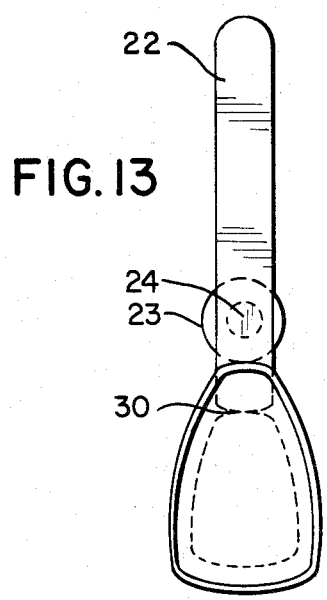
FIG. 13 is a front view of another embodiment of the invention.
Figure 14:
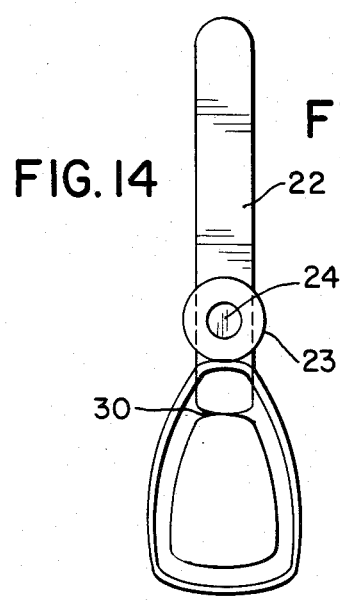
FIG. 14 is a rear view through the median plane of the embodiment as seen in FIG. 13.
Figure 15:
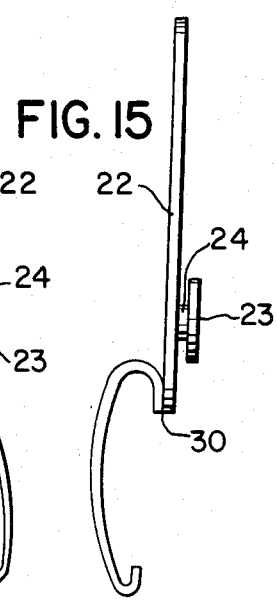
FIG. 15 is a side view through the median plane of the embodiment seen in FIG. 13.
Figure 16:
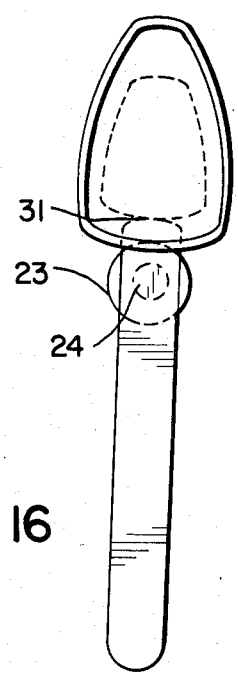
FIG. 16 is a front view through the median plane of another embodiment of the invention.
Figure 17:
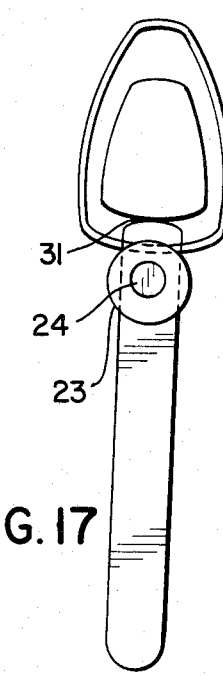
FIG. 17 is a rear view through the median plane of the embodiment of FIG. 16.
Figure 18:
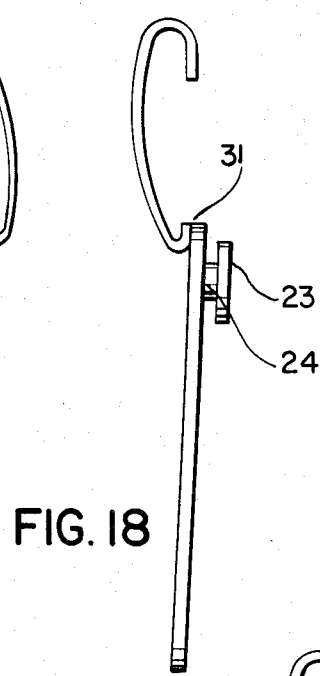
FIG. 18 is a side view through the median plane of the embodiment of FIG. 16.

The handle with attached anchor may be separately formed as in FIGS. 8, 9 & 10, preferably of plastic material, or alternatively, may be made in one piece as an integral part of the mold blank as shown in FIGS. 13, 14 & 15 or as in FIGS. 16, 17 & 18. In the one piece version, the handle would be made of the same material as the mold blank. It would be joined to the mold blank at either the cervical end 30 as depicted in FIGS. 13, 14 & 15 or at the incisal end 31 as depicted in FIGS. 16, 17 & 18. This joint could be scored or perforated so that separation of mold from the head and handle could be easily accomplished. In all cases, the handle should be of sufficient thickness to provide enough rigidity to allow it to be handled easily by the dentist. Identifying indicia may be written or impressed on the face of the handle.

Figure 11:
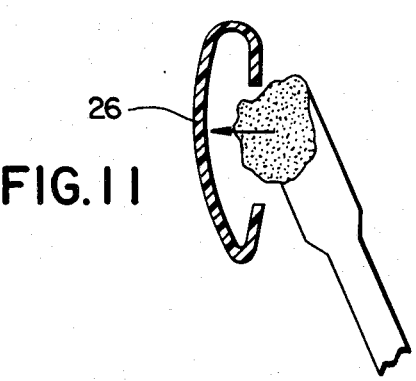
FIG. 11 is a side cross-sectional view showing the filling material being placed into a mold blank with a small spatula or other dental instrument.
Figure 12:
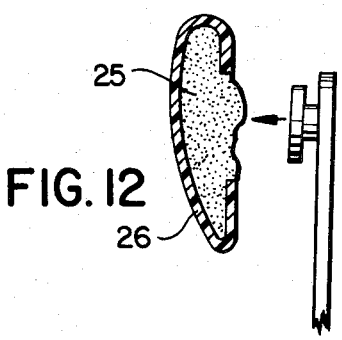
FIG. 12 shows a side view of the handle being placed into the mold blank shown in cross-section containing filling material.
Figure 19:
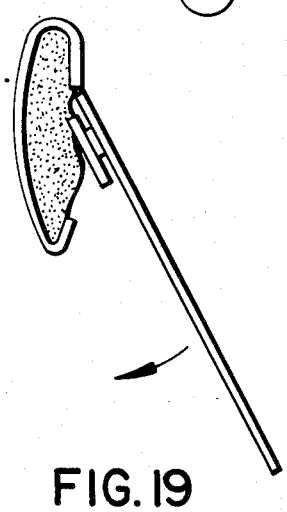
FIG. 19 is a side view through the median plane showing how the handle of the embodiment of FIGS. 13, 14 and 15 is rotated into the mass of filling material in the mold blank.
Figure 20:
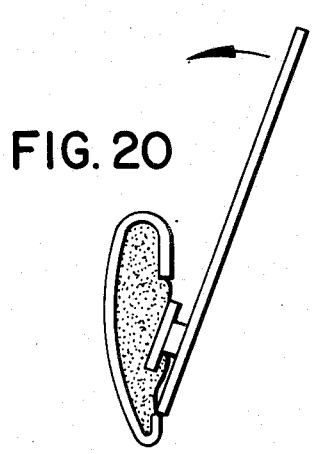
FIG. 20 is a side view through the median plane showing how the handle of the embodiment of FIGS. 16, 17 and 18 is rotated into the mass of filling material in the mold blank.
Figure 21:
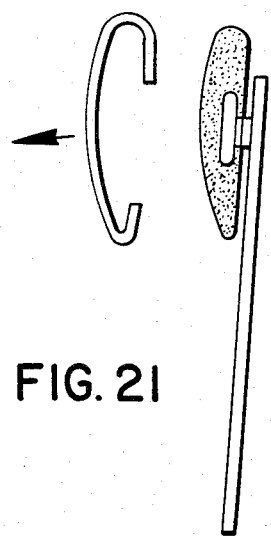
FIG. 21 is a side view through the median plane showing the removal of the mold blank away from the hardened filling material which is retained on the handle, resulting in the fully assembled device of each of the embodiments.

With the components in hand, a shade tab is created by the dentist. The dentist fills the mold blank 26 through the rear opening 29 with the filling material of a given shade or combination of shades from his stock supply. The filling material is placed into the mold blank as in FIG. 11 by a spatula or other dental tool so that the mold is substantially filled. While the material is still in the uncured and plastic flowing state, the anchor button of the handle is placed into it through the rear opening of the mold, so that the button 23 is fully submerged in the material. FIG. 12 shows how this is accomplished when mold blank and handle are separate components. FIGS. 19 & 20 show how this is accomplished when the mold blank and handle are integral and of one piece construction as in the embodiments of FIGS. 13, 14 & 15 and FIGS. 16, 17 & 18.

Once the anchor is inserted, the filling material is compressed within the mold so that voids and gaps are eliminated. Excess material forced out through the opening 29 should be smoothed flat with a small spatula or other dental instrument. In this condition the material 25 is then left to auto-polymerize or is cured by light, depending on the nature of the material.

Since none of the conventional filling materials bond to the materials of which the invention is likely to be made, it would be possible, once the filling material head 25 has hardened, to turn or twist the head about the axis of the stem 24 of the anchor. Some dentists might desire to have the head swivel freely about the stem axis relative to the handle so as to position the head more selectively in the mouth. In the event that a filling material 25 might bond to the anchor, a dentist could lightly lubricate the anchor with petrolatum or similar substance just prior to inserting the anchor into the filling material.

Once the filling material 25 has been allowed to completely harden, its form and color become unchangeable. It may be desirable to remove the transparent mold covering from the hardened filling material to eliminate possible reflection or other undesirable optical effects caused by the mold surface. This is accomplished by simply peeling the mold 26 away from the filling material. The mold must be additionally separated from the handle to which it is joined in the embodiments in which the mold and handle are integral and are of one piece construction. When the mold covering 26 is removed, the custom shade guide tab as seen in FIGS. 1, 2 & 3 is completed.

Additional shade guide tabs are made for each pure shade of filling material the dentist stocks, or any combination of those shades which might be desired. The dentist thereby produces a series of tabs of various tooth color shades, which may be mounted by the handles in a holder or display mount and used in the same manner as one uses conventional shade guides. The entire series is viewed and a comparison is made to the shade of the tooth to be repaired. Once a shade tab is provisionally selected, it may be removed from the holding mount and held by the handle next to the tooth to be repaired for a more precise comparison.

The code on the handle of the tab selected will indicate the corresponding filling material to be used to obtain the perfect match in repairing the tooth. In the event that a dentist cannot match a tooth with one of the custom shade tabs he has on hand, any new formulation of combined colors which turns out to be a successful match, can be preserved by making a new tab at that time and saving it for future reference. Thus, the subtleties and variations of shades within this system can be continually expanded.

The present invention places directly into the hands of the dentist the means for easily overcoming the problems inherent in the conventional shade guides, which arise from the discrepancy between the color of the guide tab and that of the actual repair material used by the dentist. This provides the dentist with greater precision in choosing his raw materials since the color the dentist sees in the shade guide tab is exactly the same as he will get in the patient when he treats the patient and applies the same material or combination of materials to the patient's tooth.

It is thus seen from the foregoing that a simple method and device is provided by the present invention, which furnishes the dentist with the ability to fabricate a series of shade guide tabs with identical optical properties as the actual filling materials he uses. The dentist need no longer go through a long process of trial and error, which is wasteful of time and materials.

Various modifications and embodiments of the assembly have been shown and suggested and others will be apparent to those skilled in the art. Accordingly, it is intended that the disclosure not be limiting of the invention.

What is claimed:

1. An assembly for the custom formation of a dental shade guide tab comprising a hollow transparent substantially closed mold and stick-like handle, said substantially closed mold having an opening in which selected raw tooth filling restorative material is located to harden and cure in the shape of said mold, said handle having anchor means projecting through said opening and into anchoring engagement with the restorative material, and said mold being separable from said restorative material and said handle.

2. The assembly according to claim 1 wherein said mold and said handle are separated from each other 3. The assembly according to claim 1 wherein said mold and said handle are integrally formed and joined together with said jointure forming a line of reduced strength along which said handle and mold may be bent relative to each other to project said anchor means on said handle through said opening and into the restorative material in said mold and for separation thereat of said mold from the restorative material and said handle.

4. The assembly according to claim 1 wherein said anchor means being substantially button shaped has an enlarged head and a stem 5. The assembly according to claim 4, wherein said mold is of plastics and is separable from said hardened filling material.

6. The method for forming a dental shade guide comprising the steps of providing a hollow transparent plastics mold, filling the hollow of the mold with a selected raw material to cure and harden therein, providing the mold with a handle to manipulate the hardened filling material by inserting anchor means on the handle into the filling material before the material hardens to join the handle and the filling material after the filling material hardens, and removing the transparent plastic mold from the filling material after the same hardens.

7. The method according to claim 6 including the step of attaching the anchor means having the form of a substantial button shape extending from the handle at least in part into the filling material before it hardens and cures, and rotating the button in the filling material before it hardens and cures to provide a rotatable joint therebetween.

8. The method according to claim 7, forming the mold and handle separately, and inserting the anchor means into the mold through an opening in the rear thereof to receive the anchor means therethrough.

9. The method of making a dental shade guide tab comprising making a body of dental filling material in the shape of an upper incisor tooth resulting from the insertion of raw tooth colored dental filling material within a transparent mold shell, providing a handle with an anchor member integrally formed with the handle and inserting the same into the body of raw material prior to hardening so as to be anchored thereto upon hardening, allowing the material to harden within the mold shell, moving the handle relative to the body of material to provide for relative movement therebetween, removing the mold shell from the body after hardening to expose the body.

10. The method of making a shade guide tab according to claim 9, bending the handle relative to the mold shell to anchor it to the body of material in the mold, and separating the handle and mold shell from each other.

11. The method of forming a dental shade guide comprising the steps of providing a hollow transparent plastics mold, filling the mold with a selected raw material to cure and harden, providing the mold with a handle to manipulate the hardened filling material, attaching the handle at least in part to the cured or hardened material and thereafter removing the mold to expose the cured or hardened material, and forming the mold and the handle unitary with a separable joint and providing the same with portions of reduced strength along their joining portions whereby the mold and handle may be separated from each other.

* * * * *